United States Patent
Des Abbayes et al.

(10) Patent No.: US 7,667,070 B2
(45) Date of Patent: Feb. 23, 2010

(54) LIPOPHILIC COMPOUNDS AND USES THEREOF

(75) Inventors: Hervé Des Abbayes, Brest (FR); Jean-Jacques Yaouanc, Locmaria Plouzane (FR); Jean-Claude Clement, Brest (FR); Karine Le Ny, Brest (FR); Claude Ferec, Brest (FR); Tristan Montier, Bohaas (FR); Pascal Delepine, Bohaas (FR)

(73) Assignees: Centre National de la Recherche Scientifique (CNRS), Paris (FR); Institut National de la Sante de de la Recherche Medicale (INSERM), Paris (FR); Universite de Bretagne Occidentale, Brest (FR); Centre Hospitalier Universitaire de Brest, Brest (FR)

( * ) Notice: Subject to any disclaimer, the term of this patent is extended or adjusted under 35 U.S.C. 154(b) by 535 days.

(21) Appl. No.: 10/534,236

(22) PCT Filed: Nov. 7, 2003

(86) PCT No.: PCT/FR03/50116

§ 371 (c)(1),
(2), (4) Date: Feb. 6, 2006

(87) PCT Pub. No.: WO2004/043970

PCT Pub. Date: May 27, 2004

(65) Prior Publication Data

US 2006/0165768 A1    Jul. 27, 2006

(30) Foreign Application Priority Data

Nov. 8, 2002 (FR) .................................. 02 14044

(51) Int. Cl.
C07F 9/22 (2006.01)
(52) U.S. Cl. .......................................... 562/10; 546/22
(58) Field of Classification Search .................... 562/10; 546/22
See application file for complete search history.

(56) References Cited

FOREIGN PATENT DOCUMENTS

JP        7228589        8/1995

OTHER PUBLICATIONS

Lanham, 1953, CAS: 47: 41353.*
Yasuda et al., 1995, CAS:124:18304.*
Floch et al., "Cation substitution in cationic phosphonolipids: a new concept to improve transfection activity and decrease cellular toxicity," *J Medicinal Chemistry*, 43:4617-4628, 2000.
Floch et al., "Phosphonolipids as non-viral vectors for gene therapy," *European Journal of Medicinal Chemistry*, 33:923-934, 1998.
Guenin et al., "Cationic phosphonolipids containing quaternary phosphonium and arsonium groups for dna trasfection with good efficiency and low cellular toxicity," *Angewandte Chemie International Edition*, 39:629-631, 2000.
Miller, "Cationic Liposomes for gene therapy," *Angewandte Chemie International Edition*, 37:1768-1785, 1998.
Yasuda, "Phosphoric acid ester derivative for silber halide photographic material and it treating agent," *Chemical Abstracts*, 124, 1996.

* cited by examiner

*Primary Examiner*—Rei-tsang Shiao
(74) *Attorney, Agent, or Firm*—Fulbright & Jaworski L.L.P.

(57) ABSTRACT

The present invention has for an object a cationic lipophilic compound of the following general formula (I):

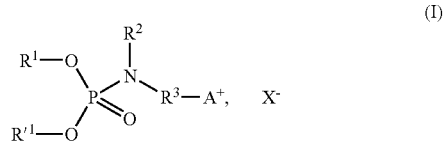

wherein:
a) $R^1$ and $R'^1$ each represent, independently from one another, an alkyl chain, an alkenyl chain or a polyalkenyl chain with from 10 to 24 carbon atoms, with the polyalkenyl chain having from 2 to 4 double links;
b) $R^2$ is a hydrogen atom or an alkyl chain having from 1 to 4 carbon atoms; and
$R^3$ is a group with the following formula (IIa) —$(CH_2)_n$— or following formula (IIb) —$C(=NH)$—$NH$—$(CH_2)_n$— wherein:
n is an integer equal to 0, 1, 2, 3 or 4; and
d) $A^+$ is an organic cation;
e) $X^-$ is an anion.

14 Claims, 6 Drawing Sheets

US 7,667,070 B2

LIPOPHILIC COMPOUNDS AND USES THEREOF

This application is a national phase application under 35 U.S.C. §371 of International Application No. PCT/FR2003/050116 filed 7 Nov. 2003, which claims priority to French Application No. 02/14044 filed 8 Nov. 2002. The entire text of each of the above-referenced disclosures is specifically incorporated herein by reference without disclaimer.

FIELD OF THE INVENTION

The present invention relates to novel lipophilic compounds showing some affinity towards nucleic acids. Such novel compounds can be used as non viral vectors for introducing a nucleic acid of interest into a selected host cell or a selected host body.

PRIOR ART

In recent years, numerous authors became interested in developing non viral vectors adapted for conveying a DNA of interest through the cell membrane and up to the cell nucleus, including within the framework of developing gene therapy methods.

In the review by A. D. MILLER entitled <<Cationic liposomes for gene therapy>> (Angewandte Chem. Int., Ed. Engl., 1998, Vol. 37: 1768-1785), being a general review on cationic lipids, it can be observed that the positive charge of the cation is always carried by a nitrogen atom.

Examples of lipophilic compounds used in the state of the art as non viral vectors include halides of 1,2-dioleyl-3-trimethylammonium deoxyglycerol, commonly so-called DOTAP, 1,2-dioleyl-3 trimethylammonium, commonly so-called DOTMA, dimethylammonium ethyloxy-carbonylcholesterol, commonly so-called DC-chol.

Phosphonolipids were also described, such as those disclosed by G. Le Bolc'h et al., (Tetrahedron Lett., 1995, 36, 6681) et V. Floch et al. (Eur. J. Med. Chem., 1998, 33, 12), phosphonolipids as an ammonium cation salt (V. Floch et al (Eur. J. Med. Chem., 1998, Vol. 33: 923-934) or as a phosphonium or arsonium cation salt (E. Guenin et al., A new. Chem. Int. Ed., 2000, Vol. 39(3); V. Floch et al., Eur. Med. Chem., 2000, Vol. 43 (24): 4617-4628).

Nevertheless, non viral cationic lipophilic vectors have a reduced DNA transfection ability in cells and show cytotoxic properties towards such cells.

There is therefore a need, in the state of the art, for non viral vectors for more efficiently conveying a nucleic acid through the cell membrane, up to the cell nucleus, so as to obtain higher transfection levels than those observed with known non viral vectors.

Another object to be reached is to obtain new non viral vectors showing an improved transfection ability combined with a low cytotoxicity for the cells to be transfected.

SUMMARY OF THE INVENTION

The Applicant has now synthesized novel cationic lipophilic compounds, of the mono- or bis-phosphoramid type, and containing a cationic part of the "Onium" type, having a high transfection ability for a nucleic acid in cells, higher than that of known non viral vectors, more particularly of known phosphonolipids.

Additionally, the novel lipophilic compounds according to the invention show reduced cytotoxicity properties compared to non viral vector compounds as disclosed in the state of the art.

An object of the invention is therefore to provide new cationic lipophilic compounds, of the mono- or bis-phosphoramid type, and containing a cationic part of the "Onium" type, as disclosed hereinafter in the detailed description of the invention. The "Onium" part of the cationic lipophilic compounds of the invention could be an ammonium, a phosphonium or an arsonium, as well as an organic cation, such as imidazolium, thiazolium or pyridinium cations.

The present invention relates to lipidic vesicles, either unilamellar or multilamellar, comprising or consisting predominantly or nearly exclusively in a lipophilic compound according to the invention, preferably as a complex between said lipophilic compound and a nucleic acid of interest.

The invention also relates to a complex formed between a nucleic acid of interest and a lipophilic compound such as defined hereinabove.

It also relates to methods for introducing, in vitro or in vivo, a nucleic acid of interest into a host cell or a host body, using a complex formed between said nucleic acid of interest and a lipophilic compound of the invention, optionally presented in the form of either unilamellar or multilamellar lipophilic vesicles.

The invention also relates to a pharmaceutical composition containing, as an active ingredient, at least one complex formed between the nucleic acid of interest and a lipophilic compound such as defined hereinabove, optionally in association with one or more physiologically compatible excipients.

In the abscissa, there are the various compounds or mixtures of compounds to be used for forming complexes with the DNA of interest before cell transfection. Between brackets the mass ratios between the lipidic compound(s) and the DNA are reported.

In the ordinates, there are the transfection efficiency results corresponding to the luciferase activity as found in the various samples of cultured transfected cells, those results being expressed in TRLU units (Total Relative Light Units), as described in the <<Materials and Methods>> section in Example 5.

Figure 1:
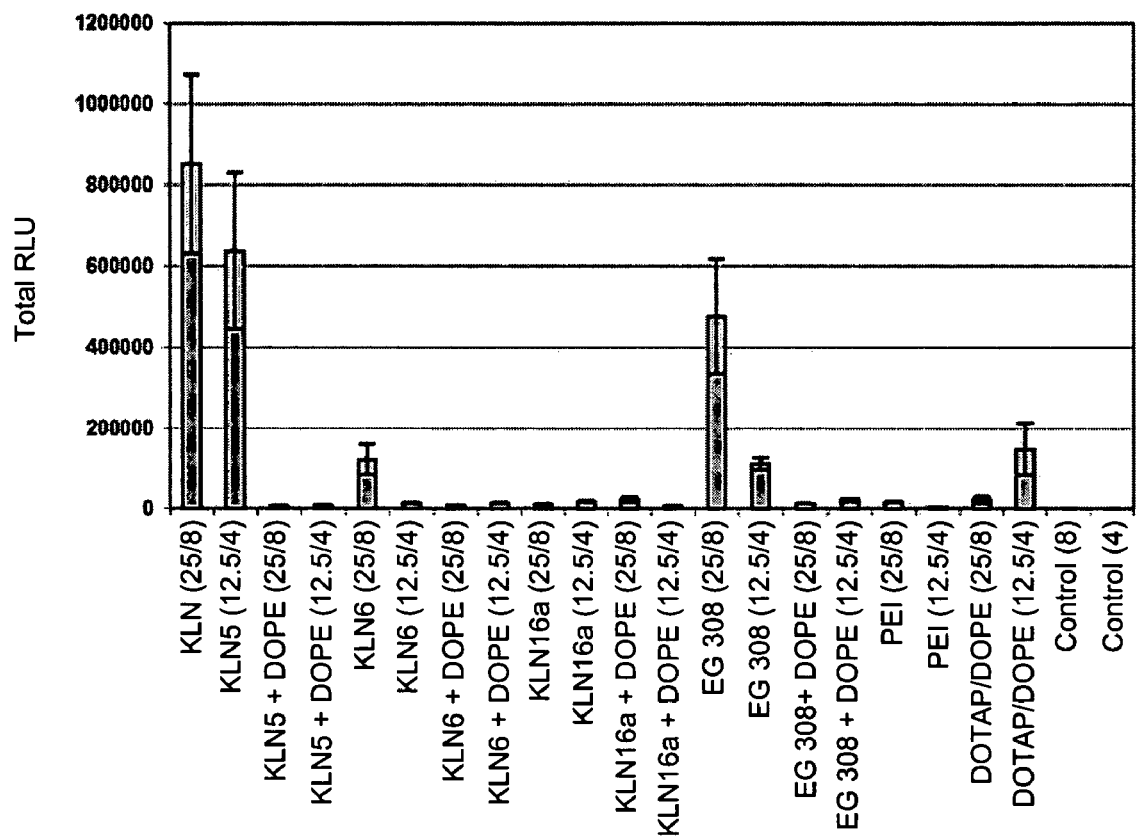
FIG. 1 illustrates the comparative results of an in vitro transfection of cells of the K562 cell lineage with prior art lipophilic compounds and lipophilic compounds according to the invention or also with a mixture of a lipophilic compound according to the invention with a lipophilic compound of the prior art. The transfection is performed with a DNA of interest coding the luciferase marker protein.
Figure 2:
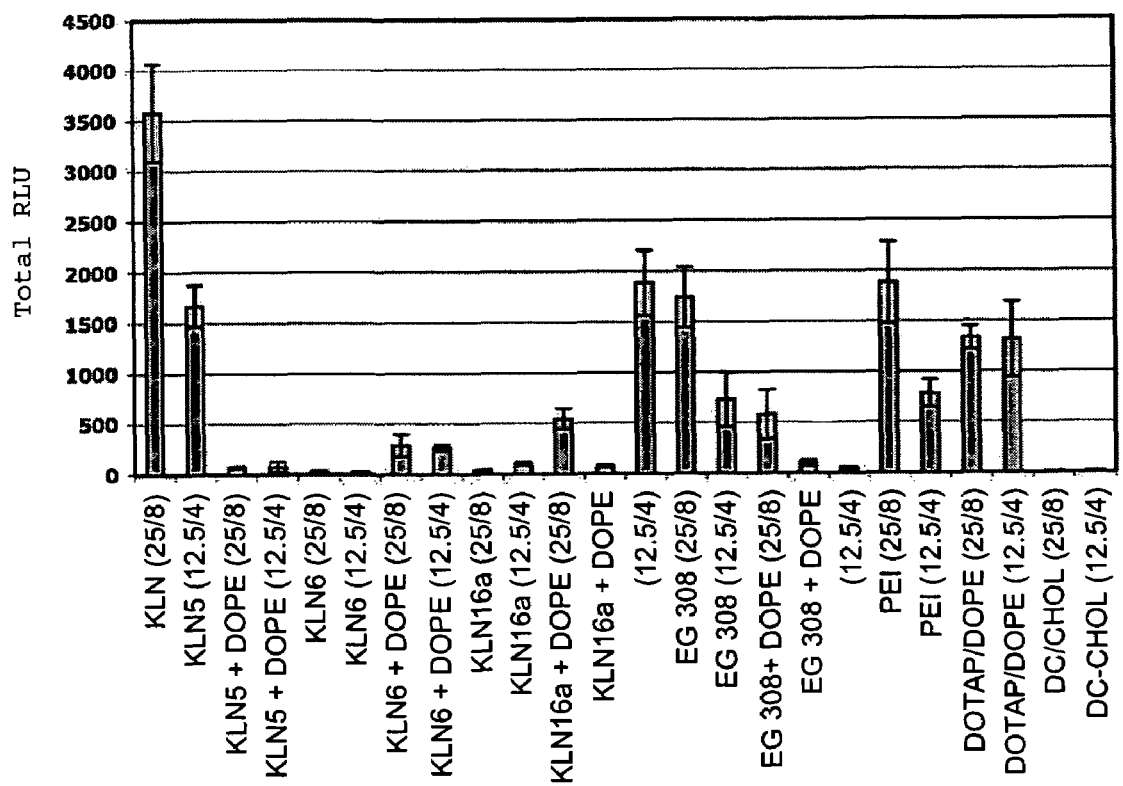

FIG. 2 illustrates the comparative results of an in vitro transfection of cells of the Jurkat cell lineage with prior art lipophilic compounds and lipophilic compounds according to the invention or also with a mixture of a lipophilic compound according to the invention with a prior art lipophilic compound. The transfection is performed with a DNA of interest coding the luciferase marker protein.

In the abscissa, there are the various compounds or mixtures of compounds to be used for forming complexes with the DNA of interest before cell transfection. Between brackets the mass ratios between the lipidic compound(s) and the DNA are reported.

In the figure, <<DC-CHOL>> means the commercial product (3β-[N-(N', N'-dimethylaminoethane)carbamoyl] cholesterol.

In the ordinates, the transfection efficiency results correspond to the luciferase activity as found in the various samples of cultured transfected cells, those results being expressed in TRLU units, as described in the <<Materials and Methods>> section in Example 5.

Figure 3:
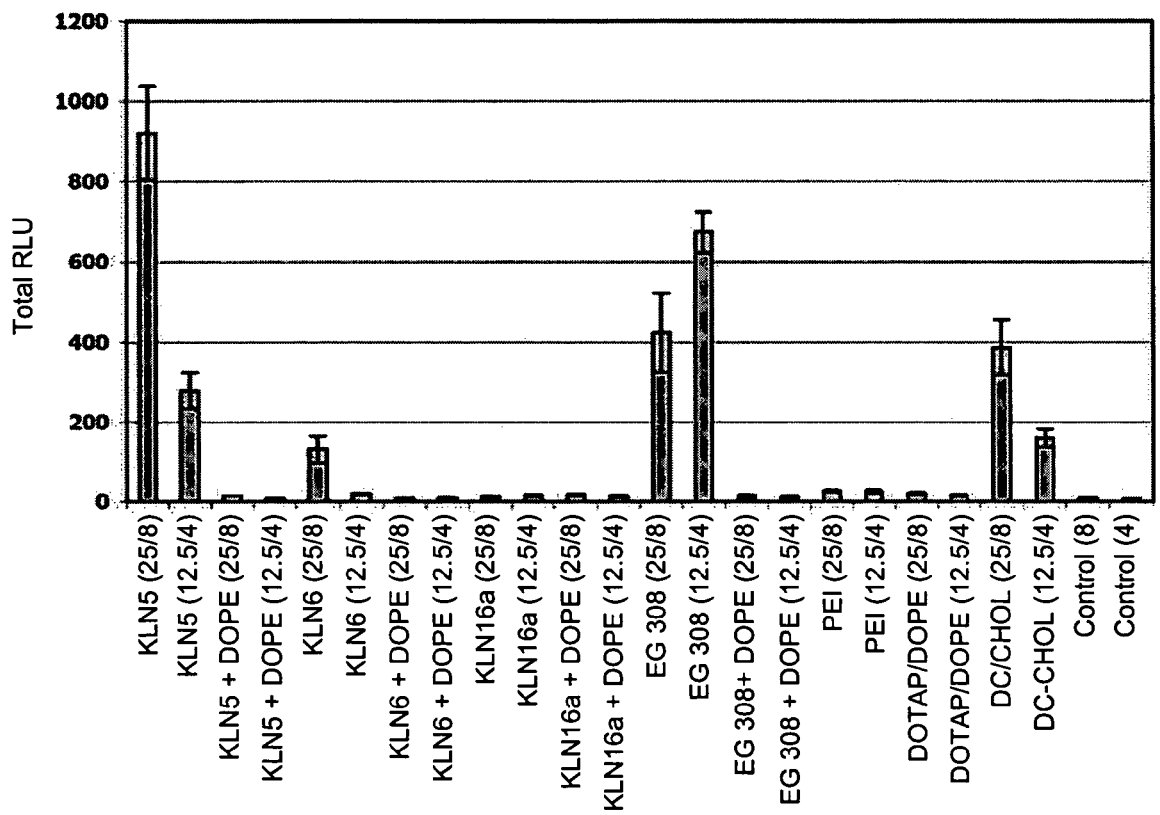

FIG. 3 illustrates the comparative results of an in vitro transfection of cells of the Daudi cell lineage with prior art lipophilic compounds and lipophilic compounds according to the invention or also with a mixture of a lipophilic compound according to the invention with a prior art lipophilic compound. The transfection is performed with a DNA of interest coding the luciferase marker protein.

In the abscissa, there are the various compounds or mixtures of compounds to be used for forming complexes with the DNA of interest before cell transfection. Between brackets the mass ratios between the lipidic compound(s) and the DNA are reported.

In the figure, <<DC-CHOL>> means the commercial product (3β-[N-(N', N'-dimethylaminoethane)carbamoyl] cholesterol.

In the ordinates, the transfection efficiency results correspond to the luciferase activity as found in the various samples of cultured transfected cells, those results being expressed in TRLU units, as described in the <<Materials and Methods>> section in Example 5.

Figure 4:
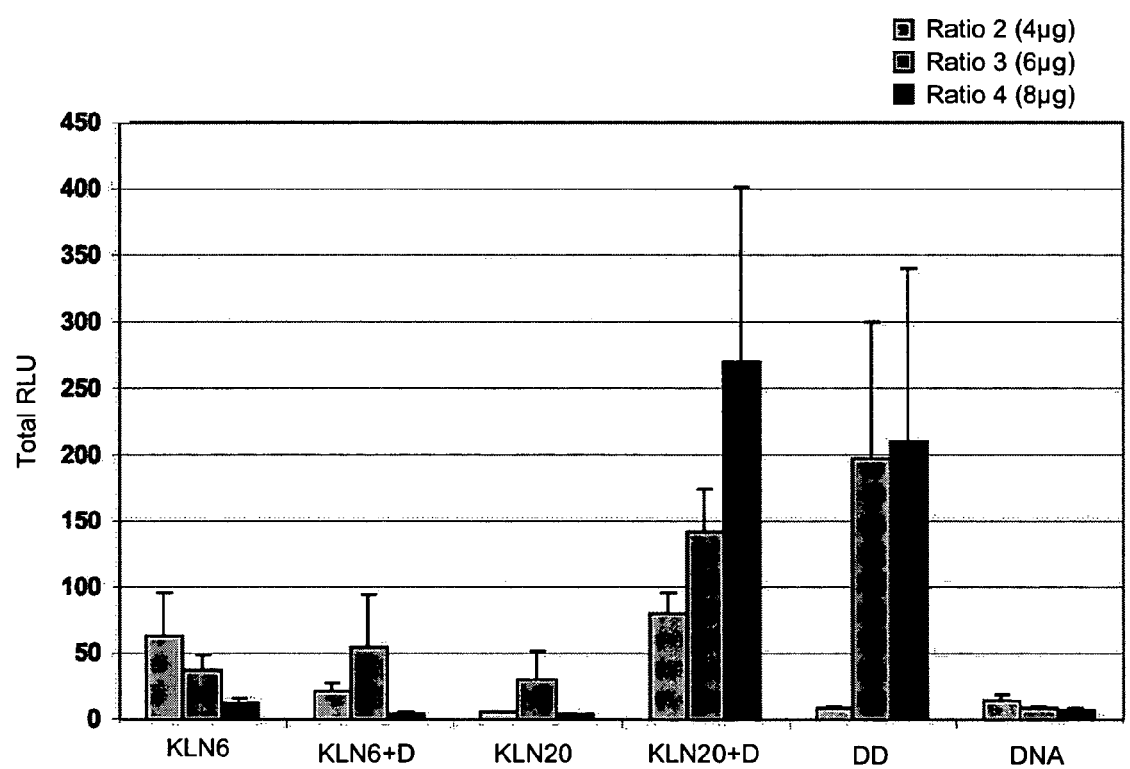

FIG. 4 illustrates the comparative results of an in vitro transfection of mouse's cardiomyocyte cells in a primary culture with prior art lipophilic compounds and lipophilic compounds according to the invention or also with a mixture of a lipophilic compound according to the invention with a prior art lipophilic compound. The transfection is performed with a DNA of interest coding the luciferase marker protein.

In the abscissa, there are the various compounds or mixtures of compounds to be used for forming complexes with the DNA of interest before cell transfection, used with three distinct charge +/charge − ratios. For example, at ratio 2, the tested composition contains twice more positive charges (lipophilic cationic compound) than negative charges (brought by DNA molecules).

In the ordinates, the transfection efficiency results correspond to the luciferase activity as found in the various samples of cultured transfected cells, those results being expressed in TRLU units, as described in the <<Materials and Methods>> section in Example 5.

In FIG. 4, <<D>> means DOPE (dioleylphosphatidylethanolamine) and <<DD>> means DOPE+DOTAP.

Figure 5:
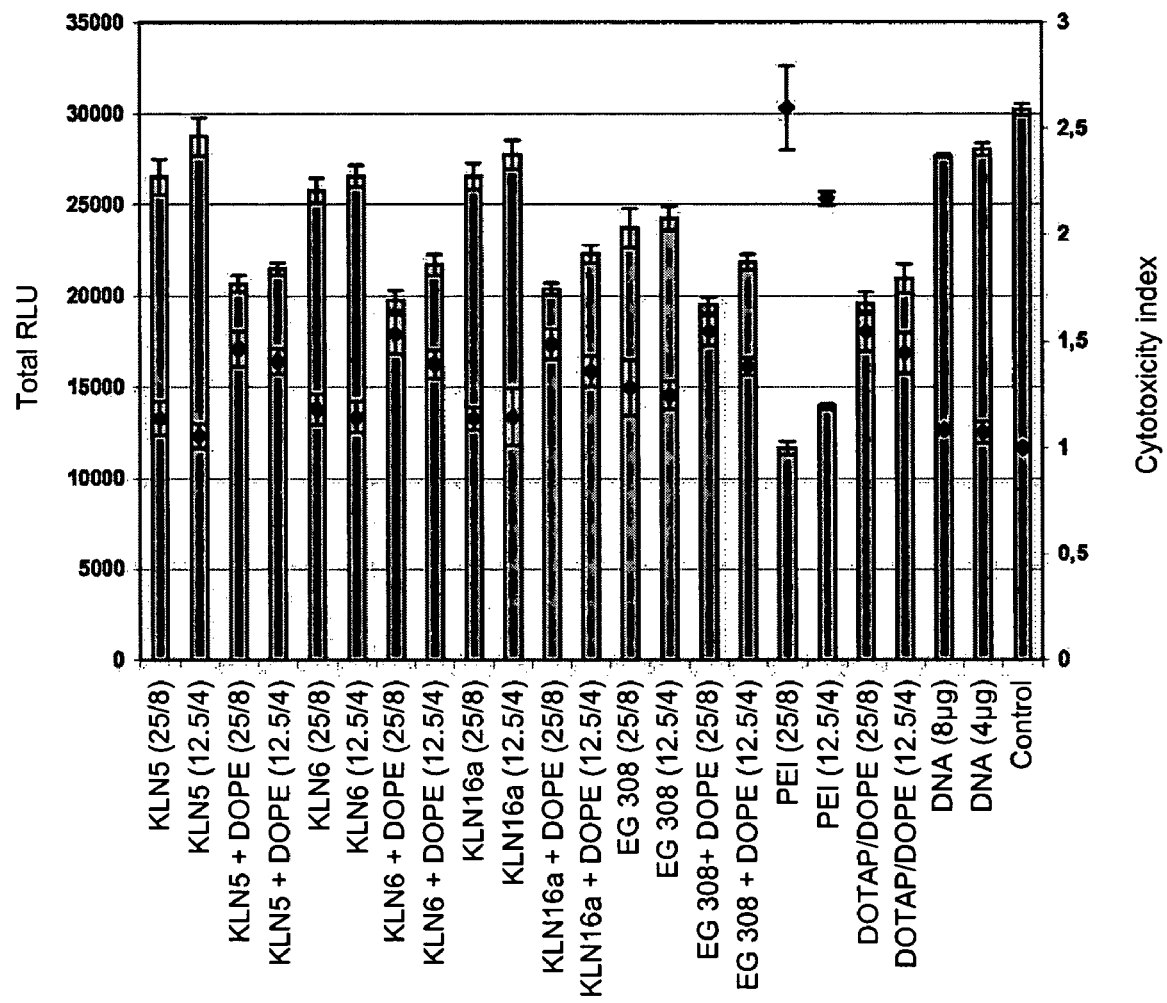

FIG. 5 illustrates cytotoxicity comparative results between different lipophilic compounds of the invention, prior art lipophilic compounds and mixtures of lipophilic compounds of the invention with prior art lipophilic compounds.

In the abscissa, there are various compounds or mixtures of compounds to be used for forming complexes with the DNA of interest before cell transfection. Between brackets the mass ratios between the lipidic compound(s) and the DNA are reported.

In the ordinates, the transfection efficiency results correspond to the luciferase activity as found in the various samples of cultured transfected cells, those results being expressed in TRLU units, as described in the <<Materials and Methods>> section in Example 5.

Figure 6:
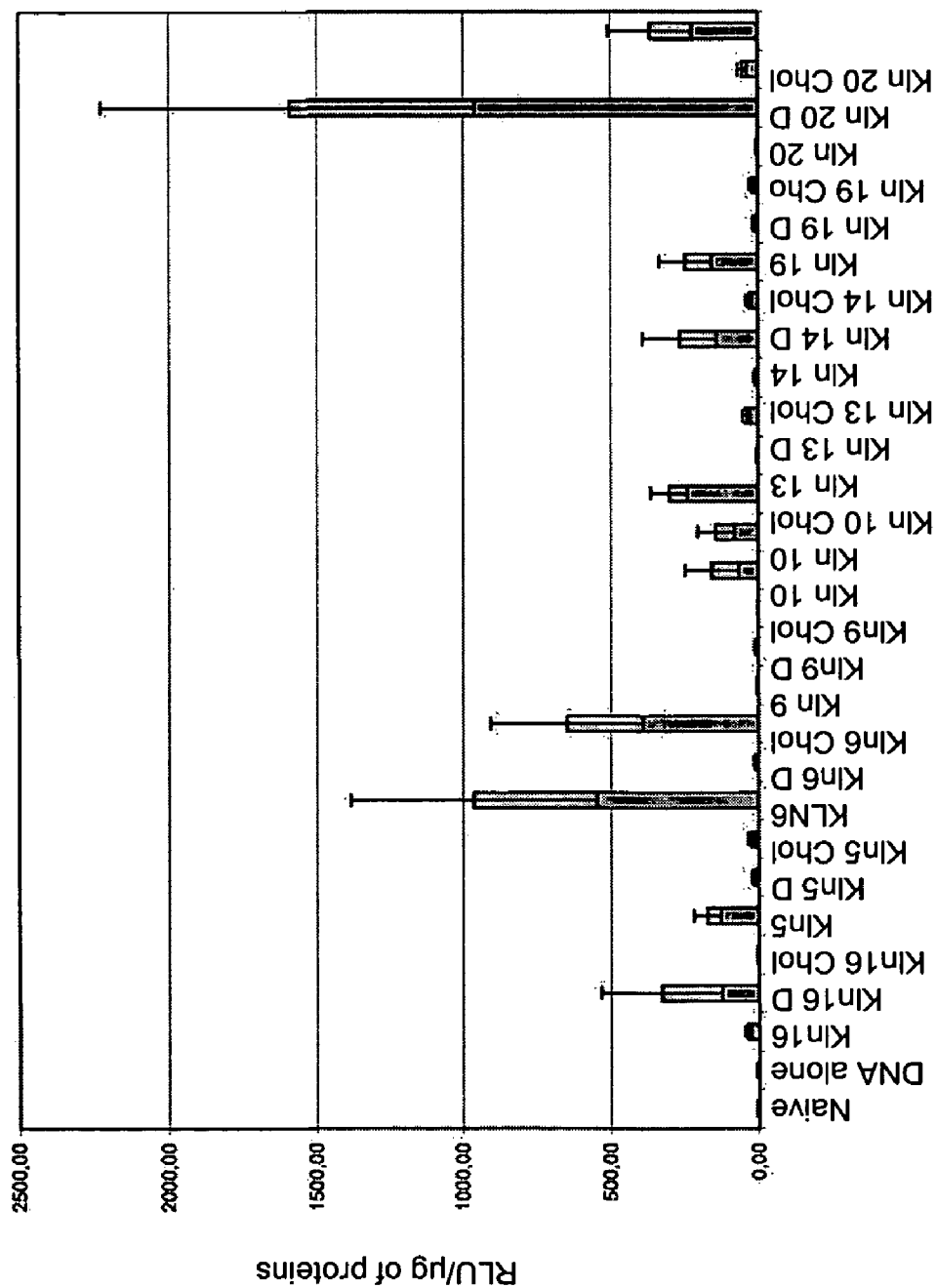

FIG. 6 illustrates the comparative results of an in vivo transfection efficiency of a DNA coding the luciferase, between different lipophilic compounds of the invention, different prior art lipophilic compounds and mixtures of lipophilic compounds of the invention with prior art lipophilic compounds.

In the abscissa, there are the various compounds or mixtures of compounds to be used for forming complexes with the DNA of interest before cell transfection. In FIG. 6, <<D>> means DOPE and <<Chol>> means cholesterol.

In the ordinates, the transcription efficiency comparative results are viewed depending on the luciferase amount as found in lungs of the sacrificed animals, those results being expressed in RLU units, as described in the <<Materials and Methods>> section in Example 6.

DETAILED DESCRIPTION OF THE INVENTION

The Applicant synthesized novel cationic lipophilic compounds, of the mono-phosphoramid or bis-phosphoramid type, and possessing a cationic part of the "Onium" type, combining a higher cell transfection ability by a nucleic acid of interest and reduced cytotoxicity properties, compared to previously known lipophilic non viral vectors.

An object of the invention is to provide a cationic lipophilic compound of the general formula (I):

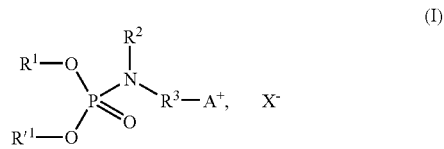

wherein:

a) $R^1$ and $R'^1$ each represent, independently from one another, an alkyl chain, an alkenyl chain or a polyalkenyl chain with from 10 to 24 carbon atoms, with the polyalkenyl chain having from 2 to 4 double links;

b) $R^2$ is a hydrogen atom or an alkyl chain having from 1 to 4 carbon atoms; and $R^3$ is a group with the following formula (IIa): —$(CH_2)_n$— or following formula (IIb): —C(=NH)—NH—$(CH_2)_n$— wherein:

n is an integer equal to 0, 1, 2, 3 or 4; and d) $A^+$ is an organic cation;

e) $X^-$ is an anion.

As used herein, <<alkyl>> means an aliphatic hydrocarbon group, which can be either linear or branched. The alkyl chain could be substituted, on one or more carbon atoms constituting it, by a group selected amongst hydroxy, alkoxy and alkylthio groups. Preferably, a carbon atom of the hydrocarbon chain comprises at the most one single substituent. Preferably, at the most, three carbon atoms of the hydrocarbon chain are substituted by at least one of the above-mentioned groups.

As used herein, <<alkenyl>> means an alkyl group containing a double carbon-carbon link, which could be located anywhere in the hydrocarbon chain.

As used herein, <<polyalkenyl>> means an alkyl group containing two to four double carbon-carbon links in the hydrocarbon chain, which could be located anywhere in the hydrocarbon chain in relative <<malonic>> positions.

As used herein, <<organic cation>> means any organic chemical group being contained in a lipophilic compound of the invention and positively charged in solution.

As used herein, <<anion>> means any organic or mineral molecule being negatively charged in solution.

Without wishing to be bound by any theory, the Applicant believes that the improved properties of the above described lipophilic compounds allowing for an efficient transfection of a nucleic acid of interest, both in vitro and in vivo, are due to the brittleness of the covalent link between the lipophilic part and the cationic part of such compounds, said link being cleaved after the lipophilic compound has passed through the cell membrane, thus releasing the cationic part maintaining the linking properties to the polyanionic nucleic acid of interest, and that could be conveyed up to the cell nucleus. The free lipophilic part, after the cleavage, could be damaged under the action of various cell enzymes, in particular the various enzymes being present in the cytoplasm.

The Applicant indeed observed, through a measurement of the $^1$H and $^{31}$P NMR spectrum, that the link between the phosphorus (P) atom and the nitrogen (N) atom of a cationic lipophilic compound of formula (I) is quickly hydrolyzed, in the absence of an enzyme, to a pH value of about 4 to 5, which is the pH found in cell intracytoplasm endosomes or lysosomes. More particularly, in the absence of any enzyme, the P—N link is completely hydrolyzed after the compound of formula (I) has been incubated for 6 hours at a pH of about 4 to 5, at a temperature of 20° C.

Preferably, $X^-$ is an anion selected amongst $CF_3CO_2$, $CF_3SO_3$, $HSO4^-$, and a halogen. More preferably, the halogen is selected amongst $Cl^-$, $Br^-$ and $I^-$.

According to a first preferred embodiment, a lipophilic compound such as defined hereinabove is characterized in that the group A is a five- to six-membered heterocyclic aromatic ring comprising a heteroatom consisting in a quaternary nitrogen linked by a covalent linking to group $R^3$.

Preferably, the heterocyclic aromatic ring comprises a second heteroatom selected amongst S or N. More preferably, when the second heteroatom is N, said second heteroatom is substituted by an alkyl chain with from 1 to 4 carbon atoms.

According to a preferred aspect of such first embodiment of a lipophilic compound, the group A is a thiazolium or an imidazolium, with the second nitrogen heteroatom optionally substituted by an alkyl chain with from 1 to 4 carbon atoms.

Preferred compounds belonging to this first embodiment of the invention include the following:
ditetradecyl 2-(1-methyl-1H-imidazol-3-ium-3-yl)ethylamidophosphate iodide [compound KLN27];
dioleyl 2-(1-methyl-1H-imidazol-3-ium-3-yl)ethylamidophosphate iodide [compound KLN28];
ditetradecyl 2-(1,3-thiazol-3-ium-3-yl)ethylamidophosphate iodide [compound KLN37];
ditetradecyl 2-(1-methyl-1H-imidazol-3-ium-3-yl)propylamido-phosphate iodide [compound KLN16a].

According to a second preferred embodiment, a lipophilic compound such as defined hereinabove is characterized in that the group A is a six-membered heterocyclic aromatic ring comprising a quaternary nitrogen heteroatom. More preferably, the group A is a pyridinium ring.

According to a preferred aspect of this second embodiment, the lipophilic compound of the invention is characterized in that the group A is represented by the following formula (III):

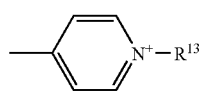

(III)

wherein $R^{13}$ represents an alkyl chain with from 1 to 4 carbon atoms.

A preferred compound belonging to the second embodiment of a lipophilic compound according to the invention is the compound:
ditetradecyl 2-(1-methyl-1H-pyridin-1-ium-4-yl)ethylamidophosphate iodide [compound KLN38].

According to a third preferred aspect, a lipophilic compound according to the invention is characterized in that the group A is a cation having the following formula (IV):

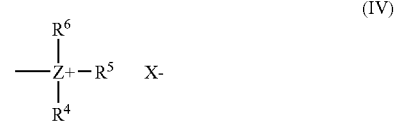

(IV)

wherein:
f) Z represents N, P or As;
g) $R^4$ and $R^5$ each represent, independently from one another, an alkyl chain with from 1 to 4 carbon atoms; and
h) $R^6$ represents an alkyl chain with from 1 to 4 carbon atoms.

It has been shown according to the invention that compounds belonging to the third above described embodiment and having a high level capacity for transfecting a nucleic acid into a target cell are preferably those for which $R^4$, $R^5$ and $R^6$ each represent a methyl group.

Preferably, $R^2$ represents hydrogen, a methyl group or an ethyl group.

Preferably, $R^3$ with formula (IIa) [—$(CH_2)_n$—] or (IIb) [—C(=NH)—NH—$(CH_2)_n$—] is such that n is an integer equal to 2, 3 or 4.

Preferably, Z represents P or $A_S$, and most preferably, Z represents $A_S$.

Preferred compounds belonging to the third embodiment of a lipophilic compound of the invention are selected amongst the following compounds:
3-[[bis(tetradecyloxy)phosphoryl](methyl)amino]-N.N.N-trimethyl-propanaminium iodide [compound KLN5];
3-[[bis(oleyloxy)phosphoryl](methyl)amino]-N.N.N-trimethyl-propanaminium iodide [compound KLN6];
3-[[bis(tetradecyloxy)phosphoryl](ethyl)amino]-N.N.N-trimethyl-ethanaminium iodide [compound KLN13];
3-[[bis(oleyloxy)phosphoryl](ethyl)amino]-N.N.N-trimethyl-ethanaminium iodide [compound KLN14];
ditetradecyl 2-(trimethylphosphonio)ethyl propylamidophosphate iodide [compound KLN 19];
dioleyl 3-(trimethylphosphonio)propylamidophosphate iodide [compound KLN20];
ditetradecyl 2-(trimethylarsonio)ethylamidophosphate iodide [compound KLN29];
dioleyl 2-(trimethylarsonio)ethylamidophosphate iodide [compound KLN30];
ditetradecyl 3-(trimethylarsonio)propylamidophosphate iodide [compound KLN31];
dioleyl 3-(trimethylarsonio)propylamidophosphate iodide [compound KLN32].

Cationic lipophilic compounds belonging to the first, second, and third above described embodiments are all compounds of the mono-phosphoramid type.

According to a fourth embodiment of the invention, an active lipophilic compound is obtained through covalently linking two compounds of the mono-phosphoramid type, both mono-phosphoramid compounds being linked together by an alkyl chain with from 1 to 4 carbon atoms, which substitutes $R^6$ group of each of both mono-phosphoramid compounds, resulting in a bis-phosphoramid compound being also encompassed by the invention.

Thus, another object of the invention is to provide a lipophilic compound of formula (I) such as defined hereinabove, said compound being characterized in that the group A is a cation of the following formula (IV):

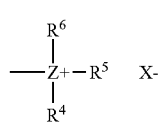

(IV)

wherein:
i) Z represents N, P or As;
j) $R^4$ and $R^5$ each represent, independently from one another, an alkyl chain with from 1 to 4 carbon atoms;
k) $R^6$ represents the group with the following formula (V):

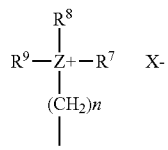

(V)

wherein:
l) $R^7$ and $R^8$ each represent, independently from one another, an alkyl chain having from 1 to 4 carbon atoms;
m) $R^9$ represents a group with the following formula (VI):

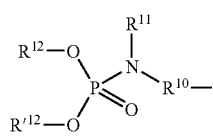

(VI)

wherein:
n) $R^{10}$ represents —(CH2)n- where n is an integer equal to 0, 1, 2, 3 or 4;
o) $R^{11}$ represents H or an alkyl group with from 1 to 4 carbon atoms; and
p) $R^{12}$ and $R'^{12}$ each represent, independently from one another, an alkyl chain, an alkenyl chain or a polyalkenyl chain with from 10 to 24 carbon atoms, with the polyalkenyl chain having from 2 to 4 double links.

Preferably, according to such a fourth embodiment for a lipophilic compound according to the invention, $R^{12}$ and $R'^{12}$ groups are identical to $R^1$ and $R'^1$ groups, respectively.

Preferably, $R^3$ and $R^{10}$ groups are identical. More preferably, groups $R^4$ and $R^5$ are identical to groups $R^7$ and $R^8$, respectively.

A preferred bis-phosphoramid compound belonging to the hereinabove fourth embodiment is the following compound:
$N^1,N^4$-bis(3-{[bis{tetradecyloxy)phosphoryl]amino}-propyl)-$N^1,N^1,N^4,N^4$-tetramethyl-1,4-butanediaminium diiodide [compound KLN39].

Generally, for the lipophilic compounds of formula (I) of the monophosphoramid type according to the invention, the groups $R^4$, $R^5$ and $R^6$ are preferably identical.

Similarly, for lipophilic compounds of formula (I) of the bis-phosphoramid type such as defined hereinabove, the groups $R^4$, $R^5$, $R^7$ and $R^8$ are preferably identical.

More preferably, for bis-phosphoramid lipophilic compounds, such as defined hereinabove, the groups $R^2$ and $R^{11}$ are identical.

As already mentioned previously, the lipidic groups $R^1$ and $R'^1$ and, for the bis-phosphoramid compounds, also the lipidic groups $R^{12}$ and $R'^{12}$, each represent, independently from one another, an alkyl chain with from 10 to 24 carbon atoms, an alkenyl chain with from 10 to 24 carbon atoms or a polyalkenyl chain with from 10 to 24 carbon atoms or a polyalkenyl chain with from 10 to 24 carbon atoms and having from 2 to 4 double links per chain.

According to a first aspect, the groups $R^1$ and $R'^1$ are identical.

According to a second aspect, the groups $R^{12}$ and $R'^{12}$ are identical.

According to a third aspect, the groups $R^1$, $R'^1$, $R^{12}$ and $R'^{12}$ are all identical.

When at least one group, amongst $R^1$, $R'^1$, $R^{12}$ and $R'^{12}$ groups, represents an alkyl chain with from 10 to 24 carbon atoms, said alkyl chain is preferably selected amongst chains with from 14 to 20 carbon atoms.

A preferred lipophilic group having an alkyl chain with from 10 to 24 carbon atoms is the tetradecyl or myristyl group, having 14 carbon atoms.

When at least one group, amongst $R^1$, $R'^1$, $R^{12}$ and $R'^{12}$ groups, represents an alkenyl chain with from 10 to 24 carbon atoms, said alkenyl chain is preferably selected amongst chains with from 14 to 20 carbon atoms.

A preferred lipophilic group possessing an alkenyl chain with 18 carbon atoms and possessing a double olefinic link is the oleyl group.

When at least one group, amongst $R^1$, $R'^1$, $R^{12}$ and $R'^{12}$ groups, represents a polyalkenyl chain, said polyalkenyl chain is preferably selected amongst chains with from 14 to 20 carbon atoms.

Preferably, the polyalkenyl chain is selected amongst $C_{18:2}$ and $C_{18:3}$ groups, wherein the first number represents the number of carbon atoms in the alkenyl chain and the second number represents the number of double links in the alkenyl chain.

Generally, the technical problem of the invention could be solved with groups $R^1$, $R'^1$, $R^{12}$ and $R'^{12}$, each group representing, independently from one another, an alkyl chain with from 10 to 24 carbon atoms, an alkenyl chain with from 10 to 24 carbon atoms or a polyalkenyl chain with from 10 to 24 carbon atoms and possessing from 2 to 4 double links par chain, as those different alkyl, alkenyl or polyalkenyl chains are all sufficiently hydrophobic for allowing a lipidic compound of the invention to contact the cell membrane, and then to enter into the cell passing through the lipidic bi-layer of the cell membrane, and to reach the nucleus passing through the nuclear membrane.

The synthesis of the various embodiments of mono-phosphoramid lipophilic compounds is further described in the Examples.

For example, for synthesizing a lipophilic compound with formula (I), wherein the group A is a cation of formula (IV) with the group $R^6$ representing an alkyl chain with from 1 to 4 carbon atoms, a phosphite compound having the following formula (VII):

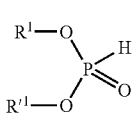
(VII)

is reacted with a diamine having the following formula (VIII):

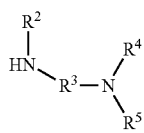
(VIII)

in the presence of an appropriate phase transfer agent, such as benzyltriethylammonium chloride, followed by the recovery of the compound of formula (I) such as defined hereinabove by quaternizing the amine $-N(R^4R^5)$ of the compound of the above mentioned formula (VIII) with an appropriate $R^6-X$ alkyl halide.

By way of illustration, in order to prepare a compound of formula (I) wherein the group A represents a five-membered heterocyclic aromatic ring comprising a heteroatom constituted by a quaternary nitrogen linked by a covalent link to the group $R^3$, such as an imidazole or thiazole heterocycle, the following synthesis method is used, exemplified for the imidazole.

a) A phosphite compound having the following formula (VII):

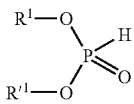
(VII)

is reacted with an amine compound having the following formula (IX):

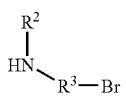
(IX)

in the presence of an appropriate phase transfer agent, such as triethyl benzylammonium chloride, in order to obtain the intermediate compound having the following formula (X):

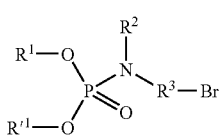
(X)

b) then the above-described compound of formula (X) is reacted with N-methyl imidazole, so as to obtain the compound having the following formula (XI):

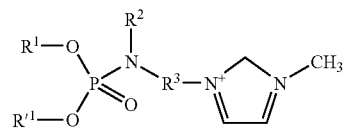
(XI)

To prepare a compound of formula (I) wherein the group A is a six-membered heterocyclic aromatic ring comprising a quaternary nitrogen heteroatom, such as pyridine, the above-defined reaction scheme is followed for compounds having a group A consisting in a six-membered heterocyclic aromatic ring and comprising a quaternary nitrogen atom.

In order to prepare a lipophilic compound of the bis-phosphoramid type according to the invention, the hereinafter described method could for example be used.

A phosphite compound of formula (VII) as described hereinabove is reacted with a diamine of formula (VIII) such as described hereinabove, in the same conditions, then 2 equivalents of the resulting compound are reacted with an equivalent of an appropriate alkyl dihalide $X-R^{10}-X$.

Generally speaking, any other conventional synthesis method could be implemented by the man of the art for preparing a mono-phosphoramid or bis-phosphoramid lipophilic compound according to the invention.

Without wishing to be bound by any theory, the Applicant believes that the cationic part of the lipophilic compound according to the invention carries the linking properties of said compound to the nucleic acid of interest, said nucleic acid being a polyanionic compound. The lipidic part of the lipophilic compound, represented by the groups $R^1$ and $R'^1$ and, for the bis-phosphoramid compounds, also by the groups $R^{12}$ and $R'^{12}$, allows for the lipophilic compound of the invention to be bound to the cell membrane, to cross through the lipidic bi-layer of the cell membrane and then to reach the cytoplasm and/or nucleus, at the level of which the nucleic acid of interest is transcribed, or even at the level of which the nucleic acid of interest hybridizes with a target nucleic acid being naturally present in the cell, either in the cytoplasm or in the nucleus.

For the purpose of the present specification, the terms <<nucleic acid>>, <<polynucleotide>> and <<oligonucleotide>> encompass DNA and RNA molecules, DNA/RNA hybrid molecules with more than two nucleotide long, indifferently in either single-strand or double-strand form.

Thus, any lipophilic compound of the invention could be used as such, preferably in solution, to be complexed with a nucleic acid of interest, the introduction of which is looked for through transfection into a host cell.

According to a fifth preferred embodiment of the invention, a lipophilic compound according to the invention is implemented in the form of lipidic vesicles, which are subsequently contacted with a nucleic acid of interest so as to form a complex between said nucleic acid and the thus prepared lipidic vesicles.

According to a first preferred aspect, the lipidic vesicles are prepared using exclusively a mono-phosphoramid or bis-phosphoramid lipophilic compound of the invention. According to said first aspect, the lipidic vesicles could be prepared from a mixture of several lipophilic compounds of the invention, preferably at the most four, and most preferably two distinct lipophilic compounds according to the invention.

Also are encompassed in the invention, lipidic vesicles comprising a mono-phosphoramid or a bis-phosphoramid lipophilic compound selected amongst the above-defined compounds.

Also are encompassed in the invention, lipidic vesicles essentially consisted of one or more mono-phosphoramid or bis-phosphoramid lipophilic compounds such as above-defined. As used herein, <<essentially>>, means lipidic vesicles comprising at least 90% by weight of one or more of a plurality of lipophilic compounds of the invention.

Are also encompassed in the invention, lipidic vesicles exclusively consisted of one or more mono-phosphoramid or bis-phosphoramid lipophilic compounds such as above-defined.

According to a second preferred aspect, the lipidic vesicles are prepared using a mixture of at least one lipophilic compound of the invention with at least one lipophilic compound which is not encompassed by the invention, most preferably a lipophilic compound fixing to a nucleic acid and useful as a non viral vector of a nucleic acid of interest. Such a non viral vector lipophilic compound is for example a state of the art lipophilic compound, such as DOPE, DOTAP, DOTMA, or cholesterol. Such lipidic vesicles comprise at the most four, and more preferably, at the most two, distinct lipophilic compounds according to the invention. Similarly, such lipidic vesicles comprise at the most four, and more preferably at the most two, distinct lipophilic compounds which are not encompassed by the invention. Most preferably, the lipidic vesicles as encompassed in the second preferred aspect of the above-mentioned fifth embodiment respectively comprise one single lipophilic compound of the invention, in admixture with one single lipophilic compound which is not encompassed by the invention. In such vesicles, the proportions of the different lipophilic compounds are variable. When the vesicles comprise a lipophilic compound of the invention and a lipophilic compound which is not encompassed by the invention, a weight ratio of the compound of the invention to another lipophilic compound ranging between 10:1 and 1:2, advantageously between 6:1 and 1:1, and most preferably between 4:1 and 1:1, is preferred.

According to this second preferred aspect of the above-mentioned fifth embodiment, are also encompassed by the invention lipidic vesicles comprising at least a mono-phosphoramid or a bis-phosphoramid lipophilic compound of the invention and at least another lipophilic compound.

According to a third aspect of the above-mentioned fifth embodiment of the invention, the lipidic vesicles are present as unilamellar lipidic vesicles, specifically small unilamellar vesicles.

According to a fourth aspect, the lipidic vesicles are in the form of multilamellar lipidic vesicles.

The lipidic vesicles according to the invention could be prepared by any technique known to the man of the art, for example, by a preliminary dissolution of the lipophilic compound(s) in a solvent, such as an aqueous medium, for example, a pyrogen-free distilled water or a physiologically compatible saline solution, followed by a sonication of the thus obtained solution.

Once prepared, the lipidic vesicles of the invention could be stored at the long term, for example, in a deep frozen form in liquid nitrogen. However, an extemporaneous preparation of such vesicles is preferred, at the most a few hours, for example, at the most 4 hours, before being contacted or incubated with a nucleic acid of interest.

According to a sixth preferred embodiment of the invention, the nucleic acid of interest to be introduced into the host cell codes a protein or a peptid. The protein could be any protein useful for implementing a genic therapy method, preferably, a somatic genic therapy, and encompasses, without any limitation, cytokins, structure proteins, hormones, antigens, immunogens, receptors, etc.

According to a second preferred aspect of the above-mentioned sixth embodiment, the nucleic acid of interest codes a sense or an antisense polynucleotide hybridizing with a target nucleic acid coding a protein the expression inhibition of which in a host cell is being sought for.

According to another preferred aspect, the nucleic acid of interest consists in a recombinant vector, preferably an expression recombinant vector, into which the nucleic acid of interest is inserted, with its coding sequence being placed under the control of regulatory sequences, including a promotor or an enhancer sequence, required for the expression of said nucleic acid of interest in the transfected host cell.

According to the invention, the nucleic acid of interest, being linear of circular, single-strand or double-strand, is first complexed with a mono-phosphoramid or a bis-phosphoramid lipophilic compound of the invention, before being inserted in the form of the complex into the host cell.

As previously described, the complexes are preferably formed through an incubation of the nucleic acid with the above defined lipidic vesicles.

However, in some cases, the complexes could be formed by incubating the nucleic acid of interest with a lipophilic compound of the invention, or a mixture of several lipophilic compounds of the invention, the complexes thus formed being subsequently used for transfecting host cells. Alternatively, lipidic vesicles, either unilamellar or multilamellar, are formed from preliminarily prepared complexes of nucleic acid/lipophilic compound(s), then the vesicles are used for transfecting the host cells.

Preferably, the complexes formed between molecules of nucleic acid and molecules of lipophilic compounds comprise a nucleic acid/lipophilic compound weight ratio ranging between 0.5 and 100, advantageously, between 1 and 100, and more preferably, between 2 and 5.

Another object of the invention is also a lipophilic compound or a lipidic vesicle such as hereinabove defined for inserting, in vitro or in vivo, a nucleic acid into a host cell or into a host body.

The invention also relates to a method for inserting, in vitro or in vivo, a nucleic acid into a host cell or into a host body, characterized in that it comprises the following steps of:

a) contacting said nucleic acid either with a lipophilic compound or with a lipidic vesicle such as hereinabove defined, so as to obtain a complex between said nucleic acid, on the one hand, and said compound or said lipidic vesicle, on the other hand;

b) incubating the host cell with the complex formed in step a), or administering, preferably through injection, the complex formed in step a) to the host body.

Preferably, said host cell is a non human mammalian cell or a human cell.

Preferably, the host body is a human being or a non human mammal, although it is not to be excluded to apply the above described method to other higher bodies, such as plants.

The invention also relates to a complex formed between a nucleic acid and a phosphoramid or a bis-phosphoramid lipophilic compound or a lipidic vesicle such as defined hereinabove.

The invention also relates to a composition comprising a complex formed between a nucleic acid and a phosphoramid or a bis-phosphoramid lipophilic compound or a lipidic vesicle such as defined hereinabove.

As already previously mentioned, the complexes formed between a nucleic acid of interest and a lipophilic compound or a lipidic vesicle of the invention could be administered through any appropriate method allowing them to be inserted into cells of a human being or an animal, such as through injection into tissue interstitial species (heart, muscle, skin, lung, liver, intestines, etc.). Preferably, the complexes are in the form of a composition also containing a physiologically compatible carrier.

In a particular embodiment for administering complexes according to the invention, the composition containing such complexes has a form adapted to an aerosol administration, for example, for inhalation.

For injecting a complex between a lipophilic compound or a lipidic vesicle of the invention and a nucleic acid of interest, the amount of DNA, RNA, or DNA/RNA of interest for an injectable dose advantageously ranges between 0.005 mg/kg and 50 mg/kg of weight of the human being or the animal in need of a treatment. Preferably, the nucleic acid amount ranges from 0.005 mg/kg to 20 mg/kg, and most preferably, from 0.05 mg/kg to 5 mg/kg.

Obviously, the man of the art will be able to adapt the nucleic acid amount in an injection dose depending on the pathology to be treated and the injection site.

The nucleic acid amount for an injectable dose is determined by the man of the art.

Another object of the invention is also a method for introducing in vivo a nucleic acid of interest into the cells of a host body, said method comprising the following steps of:

a) contacting said nucleic acid with a lipophilic compound or with a lipidic vesicle such as hereinabove defined, so as to obtain a complex between said nucleic acid, on the one hand, and said compound or said lipidic vesicle, on the other hand;

b) administering the complexes formed in step a) to said host body.

As already mentioned, the host body is preferably a human being or a non human mammal, although it could be also a plant.

Generally, the complexes formed between a nucleic acid of interest and a lipophilic compound or a lipidic vesicle of the invention are present in the form of an appropriate liquid solution, such as sterile and pyrogen-free distilled water, in appropriate complex amounts. The solution could be used as such, or could contain as well one or more stabilizers, such as Tween® (20, 40, 60 or 80), NaCl or even DMPE-PEG 5000.

The present invention also relates to a pharmaceutical composition comprising a complex formed between a nucleic acid of interest and a lipophilic compound or a lipidic vesicle of the invention, optionally in association with one or more physiologically compatible carriers or excipients.

The present invention is further illustrated, without any limitation, by the following examples.

EXAMPLES

Generally, the structure of each of the novel compounds as described in the following examples has been checked through $^1H$, $^{13}C$ and $^{31}P$ nuclear magnetic resonance (NMR) spectroscopy.

Example 1

Synthesis of 3-[[bis(tetradecyloxy)phosphoryl(methyl)amino]-N,N,N-trimethylpropanaminium iodide (KLN5)

A solution of 2.37 g (5 mmols) ditetradecylphosphite, 0.581 g (5 mmols) N,N,N'-trimethyl-1,3-propanediamine and 70 mg triethylbenzylammonium chloride in 3 ml dichloromethane is added to a two phase mixture consisted of 3 ml dichloromethane, 3 ml carbon tetrachloride and 4 ml of a 20% sodium hydroxide aqueous solution, while maintaining the reaction temperature between 0° C. and 5° C.

After stirring for one hour such a mixture at a temperature ranging from 0 to 5° C., the mixture is stirred for a period of one hour at room temperature.

Then, the organic phase is washed twice with 5 ml water and then dried on magnesium sulphate. Solvents are removed.

The structure of the final product is checked through $^1H$ and $^{31}P$ NMR spectroscopy. Then, the intermediate tertiary amine is dissolved in 5 ml dichloromethane, to which is added 0.4 ml methyl iodide, which is three times in excess relative to the intermediate tertiary amine.

After stirring overnight at room temperature, the solvent is removed and the 3-[[bis(tetradecyloxy)phosphoryl(methyl)amino]-N,N,N-trimethylpropanaminium iodide compound (KLN5) is precipitated from diethyl ester and then vacuum dried until a white powder is obtained. The final reaction yield is 85%.

Example 2

Synthesis of dioleyl 3-(trimethylphosphonio)propylamidophosphate iodide (KLN20)

A solution of 2.91 g (5 mmols) dioleylphosphite, 1.095 g (5 mmols) bromopropylamine hydrobromide and 15 mg benzyltriethylammonium chloride in dichloromethane (3 ml) is slowly added to a two phase system consisted of carbon tetrachloride (3 ml), dichloromethane (3 ml) and 4 ml of a 20% sodium hydroxide aqueous solution, while maintaining the reaction temperature between 0° C. and 5° C.

Stirring is continued for one hour at a temperature ranging from 0° C. to 5° C., then stirring is continued for an additional period of one hour at room temperature.

The organic layer is washed twice with 5 ml of water and then dried on magnesium sulphate.

Solvents are vacuum removed. The crude dioleylbromopropyl-phosphoramide was obtained as an oil. The final reaction yield is 80%.

To 1 g (1.4 mmol) of the above obtained bromophosphoramid, dissolved in 5 ml tetrahydrofurane (THF), 3 ml of a 1.0M trimethylphosphine solution in THF are added under a nitrogen atmosphere.

The reaction mixture is stirred for one week under a nitrogen atmosphere at room temperature.

Then the solvent is vacuum removed and the crude phosphonium is crystallized twice from ethyl acetate. Dioleyl 3-(trimethylphosphonio)propylamidophosphate iodide is obtained (KLN20) the purity of which being higher than 99% was checked both through $^1H$, $^{13}C$ and $^{31}P$ NMR and through thin layer chromatography (CCM) ($CHCl_3$/MeOH eluent 9:1; Rf=0.21).

The final reaction yield is 60%.

Example 3

Synthesis of ditetradecyl 2-(1-methyl-1H-imidazol-3-ium-3-yl)ethylamidophosphate iodide (KLN 27)

To a solution of ditetradecylphosphite (2.37 g, 5 mmols), 3-bromopropylamine hydrobromide (1.946 g, 5 mmols) and approximately 70 mg triethylbenzylammonium chloride in 6 ml dichloromethane and 3 ml carbon tetrachloride, 4 ml of a 20% sodium hydroxide aqueous solution are added, while maintaining the reaction temperature between 0° C. and 5° C.

After stirring for one hour at a temperature ranging from 0° C. and 5° C., stirring is continued for one hour at room temperature.

As in example 1, the reaction leads to the synthesis of the bromophosphoramid intermediate with a formula $(C_{14}H_{29}O)_2P(O)$—$NHCH_2CH_2Br$.

The above-mentioned bromophosphoramid intermediate is mixed with two N-methyl imidazole equivalents. Such a mixture is heated at a temperature ranging from 40° C. to 50° C. under stirring for three days.

Then, after cooling, the reaction mixture is diluted in 15 ml dichloromethane and the imidazole excess is removed trough a treatment with a sulfonic acid resin (DOWEX 50W×8, 1 meq $H^+$/g).

Then, the solvent is vacuum removed so as to obtain the phosphoramid of the ditetradecyl 2-(1-methyl-1H-imidazol-3-ium-3-yl)ethylamidophosphate iodide (KLN 27), with a purity ≥99% determined following the same procedures as in example 2.

The final reaction yield is 84%.

Example 4

Synthesis of 5-imino-N.N.N-trimethyl-7(tetradecyloxy)-8-oxa-4.6-diaza-7-phosphadocosan-1-aminium 7-oxide iodide (KLN 67)

To 4.74 g (10 mmols) of ditetradecylphosphite are added 1.85 g (10 mmols) 2-ethyl-2-thiopseudourea hydrobromide, 1.93 mL (20 mmoles) carbon tetrachloride and 3.48 mL (20 mmoles) diisopropylethylamine while maintaining the temperature between 0 and 5° C. This temperature is maintained, under stirring, for one hour and then brought to room temperature for another hour. 1.1 g (15 mmols) N,N-dimethylethylenediamine and 20 mL toluene are then added, and refluxed for 24 hours. The toluene and the excess amines are vacuum removed. After a cold precipitation in a small quantity of diethyl ether, and washes in the same solvent, 4 g aminophosphoguanidine $(C_{14}H_{29}O)_2P(O)NH$—$C(=NH)$—$NH$—$CH_2$—$CH_2$—$N(CH_3)_2$ are obtained, that are solubilized in 50 ml dichloromethane to which 4.26 g (30 mmols) iodomethane are added. After stirring for 24 hours at room temperature, the solvent and the excess iodomethane are vacuum evaporated. The residue is precipitated in some cold diethyl ether and then vacuum dried. 4.93 g (65% yield) KLN 67 are obtained, with the formula $(C_{14}H_{29}O)_2P(O)NH$—$C(=NH)$—$NH$—$CH_2$—$CH_2$—$N^+(CH_3)_3I^-$ as a white powder having its purity checked by the procedures as described in the previous examples.

Example 5

In Vitro Transfection of a Nucleic Acid of Interest Complexed with a Lipophilic Compound According to the Invention A. Material and Methods A.1 Cell Lineages and Plasmids For the in vitro experiments, K562, JurKat, Daudi and HeLa cell lineages were used.

The cells were cultured in a RPMI-1640 medium or in a MEM culture medium supplemented with 10% foetal calf serum (SVF), 0.2 mM glutamine, 100 U/L penicillin, 100 U/mL streptomycin and 1% fungizone.

All the cells are maintained in an atmosphere at 5% $CO_2$ at the temperature of 37° C.

The plasmid to be used is the pTG11033 plasmid coding the luciferase protein under the control of the cytomegalovirus promotor (pCMV) developed by TRANSGENE Company (Strasbourg, France).

A.2 Preparation of Cationic Phosphonolipid/DNA Complexes

Each of the cationic phosphonolipids is prepared separately or in combination with the neutral DOPE lipid (marketed by SIGMA CHEMICALS Company, Saint-Quentin Fallavier, France). The phosphonolipids are formulated through mixing solutions of the different lipids in chloroform in glass tubes, then removing the chloroform through evaporation on a rotary evaporating device so as to obtain dry films of lipids.

Then sterile and pyrogen-free distilled water is added to the glass tubes, before sealing the tubes, which are then put at a temperature of 4° C. overnight.

Small unilamellar vesicles (suv) are prepared by sonicating the compounds for ten minutes in a sonicating device (marketed by PROLABO Company, Paris, France).

In order to prepare the cationic phosphonolipid/DNA complexes, the pTG11033 plasmid is first diluted in sterile and pyrogen-free distilled water, then added to the lipid solution. The cationic phosphonolipid/DNA complexes are maintained for 30 minutes at room temperature before being administered to animals or used for in vitro transfections.

Two types of preparations are made. For the first type of preparation, 12.5 µg cationic lipidic compound are mixed with 4 µg DNA (the pTG11033 plasmid). For the second type of preparation, 25 µg cationic lipidic compound are mixed with 8 µg DNA (the pTG11033 plasmid).

In addition, the complexes are formulated either (i) with a cationic lipidic compound of the invention used alone or (ii) with a mixture of a lipidic compound of the invention and DOPE (dioleoylphosphatidyl ethanolamine).

A.3. In Vitro Transfection and Test Implementing a Gene

The in vitro transfection activity of the cationic phosphonolipid/DNA complexes is tested using the 562, Jurkat, Daudi and Hela cell lineages.

The non adherent cells (K562, Jurkat and Daudi cell lineages) are cultivated in 75 $cm^2$ culture plates. For the transfection tests, the cells are seeded in 24-well tissue culture plates, at a level of 500,000 cells per well.

For the adherent cell lineage (HeLa), the cells are seeded in 24-well tissue culture plates at a level of 150,000 cells per well.

The cells are incubated in tissue culture plates for 24 hours before the transfection step and then incubated overnight in a culture incubator in a wet atmosphere at 5% $CO_2$, at a temperature of 37° C.

The cell transfection is made following the technique as described by FELGNER et al. Proc. Natl. Acad. Sci. USA, 1987, vol. 84: 7413) with the following modifications:

The appropriate amounts of cationic lipids and the PTG11033 plasmid vector are complexed in 100 µl of an OptiMEM solution (Ref. 31985-047, Gibco BRL/Life Technologies/Cergy-Pontoise, France) added with L-glutamine, sodium bicarbonate (2.4 g/l), HEPES buffer, sodium pyruvate, hypoxanthine, thymidine, a growth factor and phenol red (1.1 mg/l). The preparation is identical to that described in the above Section A.2.

100 µl of the cationic phospholipid/DNA complexes are added in each culture well.

After a period of 2.5 hours at 37° C., the cells are added with 2 ml of the appropriate culture medium.

After an additional incubation for 48 hours at 37° C., the cells are tested for the expression of the gene coding the luciferase, using a chemiluminescent kit (marketed by PROMEGA Company, Charbonnières, France). The tests are conducted following the manufacturer's recommendations.

The results are expressed in TRLU units (for <<Total Relative Light Units>>) for an average of 8 identical culture wells.

A.4. Determination of the Cell Toxicity

The relative cytotoxicity of the different cationic phosphonolipid/DNA complexes is determined as a representation of the number of living cells after the transfection experiment, measured by using a chemiluminescent test, the CYTO-LITE® test (marketed by PACKARD Company, France) following the manufacturer's recommendations.

The cell transfection is conducted following the procedure described in the above Section A.3.

On the day of the transfection, cells are seeded in 24-well plate wells at a level of:

500,000 cells per well for the non adherent cell lineages (K 562, Jurkat, Daudi); and 150,000 cells per well for the adherent cell lineages (HeLa, CFPAC cells in primary culture).

The cells are treated for the transfection as described hereinabove and incubated for another period of 48 hours.

After incubation, the cytotoxicity test is conducted following the manufacturer's recommendations.

The amount of relative light units (RLU for <<Relative light units>>) being formed is proportional to the number of living cells.

The non transfected cells are used as controls.

The final results are expressed following a toxicity index. The toxicity index represents the ratio between the number of living cells in the control cultures (without cationic lipids/DNA complex) and the number of living cells in the culture wells containing the transfected cells.

The toxicity analysis of the 3-[[bis(tetradecyloxy)phosphoryl-(methyl)amino]-N,N,N-trimethylpropanaminium iodide [compound KLN 5] shows that there is no difference between the control cell cultures and the transfected cell cultures and that, therefore, the transfection does not show any toxicity. The toxicity index increases with the cytotoxicity properties of the cationic lipid being tested.

B. Results

In this example, toxicity properties towards cationic phosphonolip/DNA complexes of the invention are compared with the cytotoxicity of lipidic vector/DNA complexes known in the art, respectively the EG 308, DOTAP and PEI (polyethyleneimine) compounds, having their formulae represented as follows:

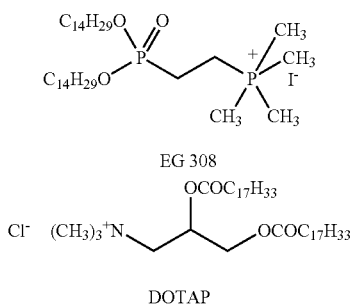

EG 308

DOTAP

—[CH$_2$—CH$_2$—NH]$_n$—

PEI

For a stringent comparative evaluation of the efficiency of cationic phosphonolips of the invention, as compared with the compounds as known in the art, each preparation of lipidic vector/DNA complexes described in Section A.2. of the hereinabove <<Material and Methods>> section is used on each of the cell lineages described in Section A.1 of the hereinabove <<Material and Methods>> Section, at the same time, and under identical conditions as those described in Section A.3 of the hereinabove <<Material and Methods>> section.

The results presented in FIGS. 1, 2, 3 and 4 show that the cationic lipidic compounds of the invention, containing a link of the phosphoramid type, are more efficient and less cytotoxic than the prior art compounds such as the EG 308 compound, and than commonly marketed transfection agents, such as DOTAP and PEI.

Example 6

Study of the In Vivo Transfection Ability of Cationic Phosphonolipid/DNA Complexes of the Invention A. Material and Methods A.1. In Vivo Transfection Through Intravenous Injection Cationic lipid/DNA complexes are prepared according to a charge (+/−) ratio of 4 and are administered to six week old mice of the Swiss lineage through one single injection into the caudal vein. Each animal receives a volume of 200 µl of a solution of the tested lipid/DNA complex, corresponding to 50 µg plasmid DNA coding the luciferase protein.

The animals are sacrificed 24 hours after the injection and each organ of interest id deep frozen in liquid nitrogen and then stored at a temperature of −70° C.

The deep frozen tissues are ground with steel balls in a 2 ml round bottom tube of the Epperdorf type using a device of the Mill MM300 mixer type (marketed by QIAGEN Company; reference: 0030120-094).

The extraction of the proteins from each tissue is performed by incubating the ground tissues in a PLB lysis buffer (Promega) followed by a centrifugation at 10,000 g, 10 min at 4° C.

The luciferase activity is tested on the lysis supernatants using the <<Luciferase Assay System>> chemiluminescence test marketed by PROMEGA Company.

The results are expressed in relative light units (RLU for <<Relative Light Unit>>).

Parallelly, the total protein concentration is measured using the <<Coomassie Plus Reagent Assay Kit>> (marketed by Pierce Company). The RLU values are standardized expressing the results by mg of total proteins.

A.2. Aerosol In Vivo Transfection

The cationic lipid/plasmid DNA complexes are prepared following the procedure described in example 5, using charge (+/−) ratios ranging from 0 to 6.

The lipid/DNA complexes are administered to six week old mice of the Swiss lineage, through inhalation of 150 µl of the solution of complexes, by means of an aerosol device. The inhalation is performed using the <<Microsprayer>> aerosol device (marketed by PENN-CENTURY, Inc. Company), allowing for the atomization to be made directly in the trachea.

Each animal receives a 50 µg dose of plasmid DNA coding the luciferase protein in the form of the lipid/DNA complex.

The animals are sacrificed 72 hours after the injection. The lungs are collected, then deep frozen in liquid nitrogen and stored at a temperature of –70° C. The extraction of proteins from the deep frozen lungs and the measurement of the RLU units by mg of proteins are performed following the procedure described in the hereinabove Section A.1.

B. Results

A comparative study of different cationic lipids is conducted by varying the linking part (Group $R^3$) between the hydrophobic domain and the hydrophilic domain, in mouse. Each lipid is evaluated separately or in admixture with the DOPE compound or cholesterol, used as co-lipids, as described in the <<Material and Methods>> section.

The results are presented in FIG. 6.

The results in FIG. 6 show the interest of transfection lipophilic compounds according to the invention, compared to state of the art lipophilic compounds or also to DNA alone.

The compounds with a hydrophobic C18:1 chain are particularly efficient for transfecting mice's lungs, whether used alone or in combination with cholesterol.

The KLN20 compound is found to be the most efficient.

The invention claimed is:

1. A cationic lipophilic compound of formula (I):

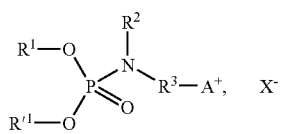

wherein:
- a) $R^1$ and $R'^1$ are independently an alkyl chain, an alkenyl chain, or a polyalkenyl chain with from 10 to 24 carbon atoms, with any polyalkenyl chain having from 2 to 4 double links;
- b) $R^2$ is a hydrogen atom or an alkyl chain having from 1 to 4 carbon atoms; and
- c) $R^3$ is a group of formula (IIa): —$(CH_2)_n$— or formula (IIb): —C(=NH)—NH—$(CH_2)_n$— wherein: n is an integer equal to 0, 1, 2, 3 or 4; and
- d) $A_+$ is an organic cation;
- e) $X^-$ is an anion;

wherein A is a cation of formula (IV):

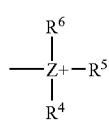

wherein:
- f) Z is N, P, or As;
- g) $R^4$ and $R^5$ are independently an alkyl chain with from 1 to 4 carbon atoms;
- h) $R^6$ is an alkyl chain with from 1 to 4 carbon atoms or is of formula (V):

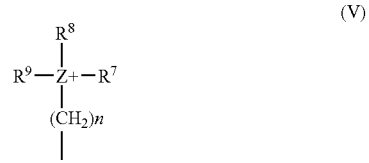

wherein:
- l) $R^7$ and $R^8$ are independently an alkyl chain having from 1 to 4 carbon atoms; and
- m) $R^9$ is a group of formula (VI):

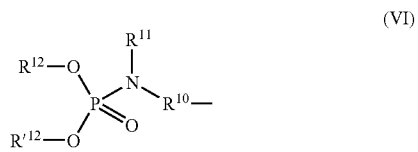

wherein:
- n) $R^{10}$ is —$(CH_2)$n- where n is 0, 1, 2, 3, or 4;
- o) $R^{11}$ is H or an alkyl group with from 1 to 4 carbon atoms; and
- p) $R^{12}$ and $R'^{12}$ are independently an alkyl chain, an alkenyl chain, or a polyalkenyl chain with from 10 to 24 carbon atoms, with any polyalkenyl chain having from 2 to 4 double links.

2. The compound of claim 1, wherein $X^-$ is an anion further defined as $CF_3CO_2^-$, $CF_3SO_3^-$, $HSO_4^-$, or a halogen.

3. The compound of claim 2, wherein the halogen is $Cl^-$, $Br^-$, or $I^-$.

4. The compound of claim 1, wherein $R^6$ is an alkyl chain with from 1 to 4 carbon atoms.

5. The compound of claim 4, wherein $R^2$ is hydrogen, a methyl group, or an ethyl group.

6. The compound of claim 4, wherein $R^3$ is further defined as having a formula (IIa) [—$(CH_2)_n$—] or (IIb) [—C(=NH)—NH—$(CH_2)_n$—] wherein n is 2, 3, or 4.

7. The compound of claim 4, further defined as:

3-[[bis(tetradecyloxy)phosphoryl](methyl)amino]-N.N.N-trimethyl-propanaminium iodide;

3-[[bis(oleyloxy)phosphoryl](methyl)amino]-N.N.N-trimethyl-propanaminium iodide;

3-[[bis(tetradecyloxy)phosphoryl](ethyl)amino]-N.N.N-trimethyl-ethanaminium iodide;

3-[[bis(oleyloxy)phosphoryl](ethyl)amino]-N.N.N-trimethyl-ethanaminium iodide;

ditetradecyl 2-(trimethylphosphonio)ethyl propylamidophosphate iodide;

dioleyl 3-(trimethylphosphonio) propylamidophosphate iodide;

ditetracyl 2-(trimethylarsonio) ethylamidophosphate iodide;

dioleyl 2-(trimethylarsonio) ethylamidophosphate iodide;

ditetracyl 3-(trimethylarsonio) propylamidophosphate iodide; or dioleyl 3-(trimethylarsonio) propylamidophosphate iodide.

8. The compound of claim 1, wherein $R^1$ and $R'^1$ are:

a tetradecyl group;

a oleyl group; or a $C_{18:2}$ or $C_{18:3}$ polyalkenyl group, wherein the first number is the number of carbon atoms in the alkenyl chain and the second number is the number of double links in the alkenyl chain.

9. The compound of claim 1, wherein $R^6$ is of formula (V):

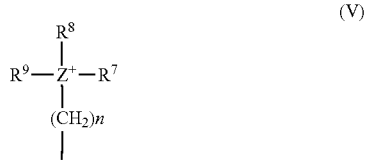

wherein:
l) $R^7$ and $R^8$ are independently an alkyl chain having from 1 to 4 carbon atoms; and
m) $R^9$ is a group of formula (VI):

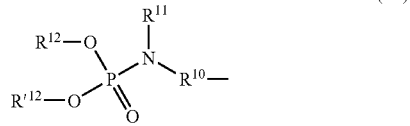

wherein:
n) $R^{10}$ is —$(CH_2)_n$- where n is 0, 1, 2, 3, or 4;
o) $R^{11}$ is H or an alkyl group with from 1 to 4 carbon atoms; and
p) $R^{12}$ and $R'^{12}$ are independently an alkyl chain, an alkenyl chain, or a polyalkenyl chain with from 10 to 24 carbon atoms, with any polyalkenyl chain having from 2 to 4 double links.

10. The compound of claim 9, wherein $R^{12}$ and $R'^{12}$ are identical to $R^1$ and $R'^1$, respectively.

11. The compound of claim 9, wherein $R^3$ and $R^{10}$ are identical.

12. The compound of claim 9, wherein $R^4$ and $R^5$ are identical to and $R^8$, respectively.

13. The compound of claim 9, further defined as $N^1,N^4$-bis (3-{[bis{tetradecyloxy)phosphoryl]amino}propyl)-$N^1,N^1$, $N^4,N^4$-tetramethyl-1,4 butane diaminium diiodide.

14. The compound of claim 9, wherein $R^{12}$ and $R'^{12}$ are independently:
a tetradecyl group;
a oleyl group; or
a $C_{18:2}$ or $C_{18:3}$ polyalkenyl group, wherein the first number is the number of carbon atoms in the alkenyl chain and the second number is the number of double links in the alkenyl chain.

* * * * *

UNITED STATES PATENT AND TRADEMARK OFFICE
CERTIFICATE OF CORRECTION

| | | |
|---|---|---|
| PATENT NO. | : 7,667,070 B2 | Page 1 of 1 |
| APPLICATION NO. | : 10/534236 | |
| DATED | : February 23, 2010 | |
| INVENTOR(S) | : Herve Des Abbayes et al. | |

It is certified that error appears in the above-identified patent and that said Letters Patent is hereby corrected as shown below:

In title page, item (75) Inventors, for the residence of Tristan Montier, delete "Bohaas" and insert --Brest-- therefor.

In title page, item (73) Assignees, in the second listed assignee, line 6, delete "de de la" and insert --et de la-- therefor.

In claim 1, column 19, line 49, delete "$A_+$" and insert -- $A^+$ -- therefor.

In claim 12, column 22, line 15, between "to" and "and", insert -- $R^7$ --.

Signed and Sealed this

Twenty-fifth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,667,070 B2 | Page 1 of 1 |
| APPLICATION NO. | : 10/534236 | |
| DATED | : February 23, 2010 | |
| INVENTOR(S) | : Hervé Des Abbayes et al. | |

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 535 days.

should read (*) Notice: Subject to any disclaimer, the term of this patent is extended or adjusted under 35 U.S.C. 154(b) by 870 days.

Signed and Sealed this

Twenty-second Day of June, 2010

David J. Kappos
*Director of the United States Patent and Trademark Office*